US006323356B1

(12) United States Patent
Löwenberg et al.

(10) Patent No.: US 6,323,356 B1
(45) Date of Patent: Nov. 27, 2001

(54) PROCESS FOR THE PREPARATION OF ALKOXYSILANES

(75) Inventors: Peter Löwenberg, Rheinfelden; Thomas Schlosser, Inzlingen; Michael Horn, Rheinfelden; Ralf Laven, Frankfurt; Jaroslaw Monkiewicz, Rheinfelden, all of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/709,459

(22) Filed: Nov. 13, 2000

(30) Foreign Application Priority Data

Nov. 13, 1999 (DE) .............................................. 199 54 635

(51) Int. Cl.$^7$ ................................. C07F 7/08; C07F 7/18
(52) U.S. Cl. ............................................................. 556/471
(58) Field of Search .............................................. 556/471

(56) References Cited

U.S. PATENT DOCUMENTS 4,298,753   11/1981   Schinabeck et al. .

5,359,114 * 10/1994  Aoki et al. ........................ 556/471 X

FOREIGN PATENT DOCUMENTS

| 1107805 | 6/1995 | (CN) . |
|---|---|---|
| 862 895 | 1/1953 | (DE) . |
| 31751 | 10/1964 | (DE) . |
| 2 033 373 | 4/1971 | (DE) . |
| 2 061 189 | 12/1974 | (DE) . |
| 24 09 731 | 5/1983 | (DE) . |
| 28 00 017 | 5/1983 | (DE) . |
| 27 44 726 | 9/1983 | (DE) . |
| 32 36 628 | 9/1986 | (DE) . |
| 198 49 196 | 4/2000 | (DE) . |
| 0 282 846 | 9/1988 | (EP) . |
| 0 741 137 | 11/1996 | (EP) . |
| 674137 | 6/1952 | (GB) . |

* cited by examiner

Primary Examiner—Paul F. Shaver
(74) Attorney, Agent, or Firm—Oblon, Spivak, McClelland, Maier & Neustadt, P.C.

(57) ABSTRACT

The present invention relates to a process for the preparation of alkoxysilanes in which at least one halogenosilane is reacted with at least one alcohol in the presence of metallic magnesium and the alkoxysilane is isolated from the crude product.

16 Claims, No Drawings

PROCESS FOR THE PREPARATION OF ALKOXYSILANES

BACKGROUND OF THE INVENTION

1. Field of the Invention

The present invention relates to a process for the preparation of alkoxysilanes.

2. Discussion of the Background

Alkoxysilanes and alkoxysilane-based compositions are used in many sectors: as adhesion promoters, crosslinking agents in polymers, as release agents, as additives in paints and coatings, for hydrophobicization of surfaces, inter alia for textiles, leather and, in particular, for the protection of buildings and facades, for the preservation of books, for particular modification of the properties of surfaces, such as coating of glass fibers or silanizing of fillers and pigments, and also for improving the theological properties of polymer dispersions and of emulsions, to name only a few examples.

Halogenosilanes and in particular, chlorosilanes, are as a rule employed for the preparation of alkoxysilanes. The reaction of a halogenosilane with an alcohol to give an alkoxysilane is known per se to the expert and is also called esterification. For example, a chloropropylmethyidimethoxysilane is obtained by reaction of a chloropropylmethyidichlorosilane with methanol, hydrogen chloride being liberated. Even after purification of the product by distillation, however, residual halogen contents, i.e., residual amounts of acidic or hydrolyzable chloride, can undesirably remain in the alkoxysilane.

Efforts are currently being made to prepare alkoxysilanes and products which include alkoxysilanes, as well as alkoxysilane-based compositions with the lowest possible halide content. Products with the lowest possible chloride content are particularly desired. Another quality feature is the color, wherein the lowest possible Gardner/APHA color numbers according to ISO 6271 are being sought.

The above-described reaction of a halogenosilane with an alcohol is carried out either discontinuously or continuously, the hydrogen halide that is formed being converted into the gas phase or remaining bonded in the liquid phase. Customary techniques for separating off the hydrogen halide by conversion into the gas phase are stripping and distillation, including reactive distillation. Such processes are described, inter alia, in DE-A 20 61 189, U.S. Pat. No. 4,298,753, DE-A 28 00 017, DE-A 24 09 731, DE-A 27 44 726, DE-A 32 36 628, DE-A 862 895 and DD 31 751. Substantial disadvantages of these processes for separating off hydrogen halide by conversion into the gas phase include: (1) the secondary reactions of the hydrogen halide with the alkoxysilanes produced to give siloxanes in accordance with the equation:

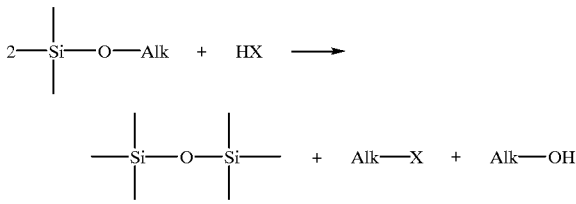

and (2) the limiting of the conversion of the halogenosilanes into alkoxysilanes by the thermodynamic equilibrium as a result of of the hydrogen halide present in the reaction mixture. This applies in particular if more than one halogen atom is to be replaced by an alkoxy radical. In such a case, non-alkoxylated and mono- and polyalkoxylated silanes are present side by side. In the reaction of trihalogenosilanes with alcohol, the equilibrium constants decrease from the first to the third stage. This means that in particular the third alkoxy group is difficult to introduce, or that third alkoxy groups introduced readily react with hydrogen halide to re-form a halogenosilane structure.

A desirable alkoxysilane is 3-chloropropyl-methyl-dimethoxysilane (CPMDMO), which is formed from 3-chloropropyl-methyl-dichlorosilane and methanol. Here also, the reaction product of the first stage, the monoalkoxychlorosilane, is favored over the dialkoxysilane. This is shown by a comparison of the equilibrium constants, that of the first stage being significantly greater than 1 at room temperature, but that of the second stage being only 0.4. According to conventional methods, the reaction is carried out discontinuously in a stirred tank reactor and the hydrogen halide formed is separated off from the reaction mixture by distillation. The yield is about 60%. It can be increased to 65% by addition of methanolic sodium methylate solution, but with the accompanying disadvantages that: (1) sodium chloride is obtained; and (2) the risk of a 3-methoxypropyl group being formed from the 3-chloropropyl group in a Williamson synthesis.

The abovementioned disadvantages of the processes in which the hydrogen halide formed is converted into the gas phase are therefore particularly serious because the passage of the hydrogen halide from the liquid phase into the gas phase takes place relatively slowly and the mass transfer of the hydrogen halide thus decisively determines the overall process. The equilibrium therefore shifts only comparatively slowly in favor of the desired alkoxylated products; and the hydrogen halide promotes the formation of siloxanes in accordance with the above equation. The hydrogen halide passes into the gas phase particularly slowly in the case of reactions with methanol, since it is readily soluble in methanol. As a result of the slow passage of the hydrogen halide into the gas phase, the yields of alkoxysilane are reduced.

Another technique, which has already been mentioned in connection with the synthesis of 3-chloropropylmethyidimethoxysilane, for removing the hydrogen halide formed from the reaction mixture is bonding thereof in the liquid phase by reaction with basic substances. If acid-binding agents are employed, for example ammonia or (tertiary) amines (DE-A 913 769, in which the removal of hydrogen chloride with ammonia is described) or alcoholates, however, stoichiometric amounts of salt are obtained, and these usually have to be separated off from the product at great expense.

The use of solvents in the removal of the hydrogen halide is also described. The solvents serve here to reduce the viscosity of the constantly single-phase reaction mixture (DE-A 20 61 189) or to lower the boiling point of the constantly single-phase reaction mixture (DE-A 28 00 017, DE-A 32 36 628).

On the other hand, it is known that it is advantageous to choose a reaction temperature of <100°C. in the reaction of the halogenosilane with the alcohol, so that undesirable side reactions to give siloxanes are avoided (DE-A 24 09 731). This requires a removal of hydrogen halide from a temperature level which is as low as possible, although higher temperatures would be more favorable for this removal.

The use of various reactors is described for the preparation of alkoxysilanes, i.e., stirred tanks (for example GB 674 137), tube reactors (DE-A 20 33 373), stirred tanks with a column (for example DE-A 32 36 628) and reaction distillation columns (for example U.S. Pat. No. 4,298,753).

Processes for removing the residual halogen content from alkoxysilanes by reaction or neutralization with alkali metal alcoholates, such as, for example, sodium methanolate, and separating off the salt formed in the process are also known from EP 0 282 846 A2 and EP 0 741 137 A1. Such neutralization processes have the disadvantage that considerable amounts of product are also decomposed in this reaction. By-products are, inter alia, siloxanes, tetraalkoxysilane, addition products, such as methoxyethyltrimethoxysilanes by reaction of sodium methanolate and vinyltrimethoxysilane, methoxypropyltrimethoxysilanes formed from sodium methanolate and chloropropyltrimethoxysilane and methoxypropylmethyidimethoxysilanes from sodium methanolate and chloropropylmethyidimethoxysilane, or else, in the case of a reaction of alkali metal methanolate and an alkyltrimethoxysilane, highly toxic tetramethoxysilane.

Moreover, if customary neutralizing agents such as alkali metal alcoholates are used, a deterioration in the color number of the alkoxysilane treated is often observed.

The specifications CN 11 07 85 1A and 11 07 85 2A describe processes for the preparation of vinyltriethoxysilane and chloropropyltrimethoxysilane, which are said to give very pure products by the use of magnesium alcoholates. It is a disadvantage here that these alcoholates are difficult to handle since they are very sensitive to moisture. Furthermore, magnesium alcoholates are in powder form and tend to form lumps, which in turn makes accurate metering of this substance difficult. This disadvantage particularly relates to the metering into heated or hot products, which is usually carried out in practice, because the silane or other volatile constituents of the reaction formulation condense on the magnesium alcoholates, incipiently dissolve them and therefore convert them into a form which is no longer free-flowing.

To avoid this disadvantage, attempts have been made to employ alcoholic solutions of said alkaline earth metal alcoholates. The undesirable result, however, is that considerable amounts of alcohol are introduced into the neutralization step and must be separated off again by distillation, consuming time and energy. Furthermore, the magnesium alcoholates are expensive and are available in industrial quantities to only a limited extent.

The German Patent Application 198 49 196.4, which has not yet been published, discloses a process for neutralizing and decreasing the residual halogen content in alkoxysilanes or in alkoxysilane-based compositions, an alkoxysilane which has a residual content of acidic halide being subsequently treated with metallic magnesium in the presence of an alcohol. Such additional measures for after-treatment of products are as a rule complex and necessitate additional costs. It has furthermore been found in the reaction of chlorosilanes with alcohol that the alcohol reacts with the hydrogen chloride liberated and siloxanes are formed with progressive esterification. A high siloxane content is also to be recorded at an increased hydrogen chloride solubility in the system. These side reactions, which take place before the concluding neutralization step, have hitherto been controllable only with difficulty and lead to moderate yields because of the low selectivity.

SUMMARY OF THE INVENTION

One object of the present invention is to provide a method for producing alkoxysilanes that avoids the problems of the conventional methods described above.

Another object of the present invention is to provide a process in which alkoxysilanes may be effectively prepared.

Another object of the present invention is to provide a process prepare alkoxysilanes with the lowest possible content of residual halogen.

These and other objects have been achieved by the present invention, the first embodiment of which provides a process for the preparation of alkoxysilanes, which process includes:

reacting at least one halogenosilane with at least one alcohol in the presence of metallic magnesium to form a crude product; and isolating an alkoxysilane from the crude product.

DETAILED DESCRIPTION OF THE INVENTION

Various other objects, features and attendant advantages of the present invention will be more fully appreciated as the same becomes better understood from the following detailed description of the preferred embodiments of the invention.

Surprisingly, it has been found that a direct reaction of chlorosilane with alcohol to give alkoxysilane takes place in the presence of metallic magnesium, the hydrogen chloride formed during the esterification and remaining in solution being bonded in an advantageous manner by an "in situ" neutralization which runs in parallel, to form magnesium chloride, and that the side reactions and by-products which are known per se and are to be expected were not observed.

Surprisingly, a particularly product-protecting effect of the reaction according to the invention is also to be found, this still allowing high conversion rates even under drastic conditions, such as elevated temperatures, a large excess of alcohol and long reaction times.

It is thus surprising that in the reaction according to the invention, preferably of chlorosilane and alcohol, an optimum and product-protecting equilibrium is as a rule established for the resulting alkoxysilane, and a very low concentration of hydrogen chloride in the crude product is achieved here. In the subsequent course of the esterification also, in general no formation of by-products is observed. It is believed that direct neutralization of hydrogen chloride starts automatically in the present process when the equilibrium of the reaction wants to shift to the detriment of the product.

The solids contents still present in the crude product after the esterification/neutralization step, that is to say the magnesium chloride formed here and any unreacted metallic magnesium present in excess, can be separated off in a simple manner, preferably by filtration. Products with contents of high-boiling components and residual halogen, in particular residual chloride contents, which are low are obtained here in an advantageous manner. Low-halogen products and alkoxysilanes with low halogen contents are in general to be understood as those in which the halogen content is <1000 ppm by weight. In particular, the halides can be so-called hydrolyzable, that is to say acidic, chlorine compounds, such as, for example, hydrogen chloride, chlorosilanes and chloroalkoxysilanes, including organofunctional chloro- and chloroalkoxysilanes.

An excess of alcohol in the product in general causes no trouble, but can be removed by distillation before or after removal of the solids if desired in the present process. The distillation can be carried out under normal pressure or reduced pressure.

When the present process is used, it is moreover observed in a similarly advantageous and surprising manner that the color number of alkoxysilanes prepared according to the invention as a rule is not impaired with respect to the color number of products available on the market which are prepared in a more complex manner.

Not least, the process according to the invention is advantageous since it offers the possibility of preparing alkoxysilanes with low residual halogen contents efficiently in a so-called "one-pot process" without an additional process also having to be carried out for neutralization of acidic chlorides, in contrast to conventional esterification processes.

The present process is also advantageous since comparatively inexpensive starting substances which are adequately commercially available can be used.

A particularly simple, economical and environment-friendly process for the preparation and simultaneous neutralization of alkoxysilanes with low contents of residual halogen can thus be provided.

The present invention thus relates to a process for the preparation of alkoxysilanes, which includes reacting at least one halogenosilane with at least one alcohol in the presence of metallic magnesium and then isolating the alkoxysilane from the crude product.

Preferably, the process according to the invention is carried out as a so-called "one-pot reaction", in which the halogenosilane and magnesium are brought together, this mixture is heated, while stirring, and the alcohol is added.

Preferably, the alcohol is employed in excess. During the reaction according to a preferable embodiment of the invention, the alkoxysilane is formed from the chlorosilane and the alcohol employed. Hydrogen chloride obtained here escapes, and only in the course of the reaction does an alcohol excess form, in which the hydrogen chloride dissolves and is bonded practically at the same time, that is to say "in situ", and as a rule is obtained as solid magnesium chloride.

The present process is preferably carried out under normal pressure or reduced pressure, for example >0.02 bar absolute. However, the process can also be carried out under increased pressure, for example <10 bar absolute. The reaction according to the invention is preferably carried out under a pressure of 0.8 to 1.3 bar absolute.

The process is preferably carried out with exclusion of water. The reaction is suitably carried out under the cover of an inert gas, for example under nitrogen. When the reaction has ended, the solids content present in the crude product can be separated off. The alcohol content which may still be present can be removed by distillation—if necessary. However, the pure product can also be isolated directly by distillation from the crude product obtained according to the invention. Alkoxysilanes obtained according to the invention in general have very low residual halogen values, with a simultaneously high product selectivity.

A chlorosilane is preferably employed in the process according to the invention. However, a mixture of chlorosilanes can also be employed. Fluorosilanes, bromosilanes and iodosilanes can furthermore be employed.

The following chlorosilanes are preferred in the process according to the invention: vinyltrichlorosilane, 3-chloropropyltrichlorosilane, 3-chloropropylmethyidichlorosilane, n-propyltrichlorosilane, i-propyltrichlorosilane, n-propylmethyldichlorosilane, trimethylchlorosilane, dimethyldichlorosilane, methyltrichlorosilane, ethyltrichlorosilane, n-butyltrichlorosilane, i-butyltrichlorosilane, i-butylmethyldichlorosilane, n-octyltrichlorosilane, hexadecyltrichlorosilane, cyclohexylmethyidichlorosilane, dicyclopentyldichlorosilane, 3-methacryloxypropyltrichlorosilane and fluoroalkyl- and perfluoroalkyltrichlorosilanes, such as 3,3,4,4,5,5,6,6,7,7,8,8-tridecafluoro-1,1,2,2-tetrahydrooctyltrichlorosilane, 3,3,4,4,5,5,6,6,7,7,8,8,9,9,10,10,10-heptadecafluoro-1,1,2,2-tetrahydrodecyltrichlorosilane. Mixtures are possible.

Commercially available magnesium turnings, for example from Eckart Non Ferrum (St. Georgen/A) of the type "MF 15" or "Almamet 150", can be employed, for example, in the process according to the invention. Magnesium powder or turnings in which the average particle size is preferably 20 $\mu$m to 15 mm, particularly preferably 50 $\mu$m to 10 mm, especially preferably 100 $\mu$m to 1 mm, are suitably employed. However, other magnesium variants, for example bars or tape, are also suitable.

The amount of magnesium to be employed is preferably calculated from the halide or chloride contents of the crude product to be expected in conventional processes, an excess of metal preferably being employed. The amount of magnesium is preferably chosen such that a pH in the basic range, preferably pH 10 to 14, can suitably be maintained after the reaction.

It is preferable to meter the alcohol in excess, preferably in an amount which is just sufficient to convert excess magnesium into magnesium alcoholate in an appropriate period of time.

The excess of alcohol is suitably between 0.001 and 500 mol %, preferably between 10 and 400 mol %, especially preferably between 20 and 200 mol %, based on the halogenosilane to be reacted.

Methanol, ethanol, n-propanol, i-propanol, methoxyethanol, n-butanol or i- or sec-butanol are preferably employed as the alcohol in the process according to the invention, depending on the desired esterification product.

The reaction is preferably carried out in a temperature range from 0 to 200° C., more preferably 10 to 160° C., particularly preferably between 20° C. and the boiling point of the corresponding chlorosilane or alkoxysilane.

The reaction according to the invention preferably lasts between 5 minutes and 48 hours, more preferably between 10 minutes and 24 hours, and particularly preferably for 15 minutes to 12 hours; and good thorough mixing is also preferred.

To isolate the desired product, the solids content is separated off in a suitable manner from the crude product obtained according to the invention, for example in the preparation of chloropropylmethyidimethoxysilane. The solids are preferably separated off by filtration. However, the solids can also be separated off by centrifugation. The product thus obtained can moreover be subjected to a separate distillation. However, the desired product can also be isolated by distillation of the solids-containing crude product according to the invention, the distillation preferably being carried out under reduced pressure.

The process according to the invention is particularly suitable for, though not limited to, the preparation of the following alkoxysilanes: vinyltrimethoxysilane, vinyltriethoxysilane, vinyl-tris(2-methoxyethoxy)silane, 3-chloropropyltrimethoxysilane, 3-chloropropyltriethoxysilane, 3-chloropropyl-methyl-diethoxysilane, 3-chloropropylmethyidiethoxysilane, 3-propyltrimethoxysilane, n-propyltriethoxysilane, n-propylmethyldimethoxysilane, n-propylmethyldiethoxysilane, trimethylmethoxysilane, trimethylethoxysilane, dimethyldimethoxysilane, dimethyldiethoxysilane, methyltrimethoxysilane, methyltriethoxysilane, ethyltrimethoxysilane, ethyltriethoxysilane, i-butyltrimethoxysilane, i-butyltriethoxysilane, hexadecyltrimethoxysilane, hexadecyltriethoxysilane, cyclohexyl-methyldimethoxysilane, cyclohexyl-methyldiethoxysilane, dicyclopentyldimethoxysilane, dicyclopentyldiethoxysilane, 3-methacryloxypropyltrimethoxysilane, 3-methacryloxypropyltriethoxysilane and perfluoroalkyl- and fluoroalkyl-functional alkoxysilanes, such as 3,3,4,4,5,5,6,6,7,7,8,8,8-tridecafluoro-1,1,2,2-tetrahydrooctyltrimethoxysilane, 3,3,4,4,5,5,6,6,7,7,8,8,8-tridecafluoro-1,1,2,2-tetrahydrooctyltriethoxysilane, 3,3,4,4,5,5,6,6,7,7,8,8,9,9,10,10,10-heptadecafluoro-1,1,2,2-tetrahydrodecyltrimethoxysilane and 3,3,4,4,5,5,6,6,7,7,8,8,9,9,10,10,10-heptadecafluoro-1,1,2,2-tetrahydrodecyltriethoxysilane.

The process according to the invention allows the preparation of low-halogen alkoxysilanes, i.e., those with a residual halogen content, in particular of acidic chloride, of <1000 ppm by weight, preferably <100 ppm by weight, particularly preferably <10 ppm by weight, in particular down to the detection limit, which is about ≦1 ppm by weight, in an advantageous manner—since it is simple, economical and environmentally friendly.

By the process according to the invention, a 30% or greater reduction in acidic halide content over conventional systems having a comparable expenditure is possible.

In addition, the process according to the invention allows the production of products with good color numbers in an advantageous and surprising manner.

EXAMPLES

Having generally described this invention, a further understanding can be obtained by reference to certain specific examples which are provided herein for purposes of illustration only and are not intended to be limiting unless otherwise specified.

Comparison Example A 1440 g of chloropropylmethyidichlorosilane are initially introduced into the reaction vessel and are heated up to about 60° C. 600 g of recycled alcohol (methanol from the preceding esterification) are now metered in. The mixture is heated up continuously to about 120° C. in the course of the reaction and the HCl gas formed is driven off. The temperature falls below 100° C. here. 400 g of pure methanol are then metered in. At the same time, methanol is distilled off into the recycled alcohol reservoir. The metering rate is constant at 200 g/hour over the entire period of time. A content of 40,000 ppm by weight of hydrolyzable chloride and a content of high-boiling components of 11% are determined in the crude product thus obtained. After the mixture has cooled to below 40° C., the hydrolyzable chloride is reacted with 300 g of a 30% strength sodium methylate solution and the salt formed is filtered off. Distillation gives 962 g (70%) of chloropropylmethyidimethoxysilane and 206 g of methanol. A content of hydrolyzable chloride of 1150 ppm by weight is determined in the distillate obtained. The black distillation residue (about 380 g) comprises predominantly siloxanes.

Comparison Example B 1560 g of propyltrichlorosilane are initially introduced into the reaction vessel and are heated up to about 60° C. 600 g of recycled alcohol (methanol from the preceding esterification) are now metered in. The mixture is heated up continuously to about 120° C. in the course of the reaction and the HCl gas formed is driven off. The temperature now falls to below 100° C. 1000 g of pure methanol are then metered in. At the same time, methanol is distilled off into the recycled alcohol reservoir. The metering rate is constant at 200 g/hour over the entire period of time. A content of 55,000 ppm by weight of hydrolyzable chloride and a content of high-boiling components of 9% are determined in the crude product thus obtained. After the mixture has cooled to below 40° C., the hydrolyzable chloride is reacted with 400 g of a 30% strength sodium methylate solution and the salt is filtered off. Distillation gives 1083 g (75%) of propyltrimethoxysilane and 311 g of methanol. A content of hydrolyzable chloride of 255 ppm by weight is determined in the distillate obtained. The distillation residue of about 355 g comprises predominantly siloxanes.

Comparison Example C 1440 g of propylmethyidichlorosilane are initially introduced into the reaction vessel and are heated up to about 60° C. 600 g of recycled alcohol (ethanol from the preceding esterification) are now metered in. The mixture is heated up continuously to about 120° C. in the course of the reaction and the HCl gas formed is driven off. The temperature now falls to below 100° C. 900 g of pure ethanol are then metered in. At the same time, ethanol is distilled off into the recycled alcohol reservoir. The metering rate is constant at 290 g/hour over the entire period of time. A content of 23,000 ppm by weight of hydrolyzable chloride and a content of high-boiling components of 9% are determined in the crude product thus obtained. After the mixture has cooled to below 40° C., the hydrolyzable chloride is reacted with 350 g of a 21% strength sodium ethylate solution and the salt is filtered off. Distillation gives 1195 g (74%) of propylmethyidiethoxysilane and 326 g of ethanol. A content of hydrolyzable chloride of 557 ppm by weight is determined in the distillate obtained. The distillation residue of about 408 g comprises predominantly siloxanes.

Comparison Example D 1440 g of hexadecyltrichlorosilane are initially introduced into the reaction vessel and are heated up to about 60° C. 350 g of recycled alcohol (methanol from the preceding esterification) are now metered in. The mixture is heated up continuously to about 120° C. in the course of the reaction and the HCl gas formed is driven off. The temperature now falls to below 100° C. 400 g of pure methanol are then metered in. At the same time, methanol is distilled off into the recycled alcohol reservoir. The metering rate is constant at 200 g/hour over the entire period of time. A content of 70,000 ppm by weight of hydrolyzable chloride and a content of high-boiling components of 42% are determined in the crude product thus obtained. After the mixture has cooled to below 40° C., the hydrolyzable chloride is reacted with 500 g of a 30% strength sodium methylate solution and the salt is filtered off. Distillation gives 776 g (56%) of hexadecyltrimethoxysilane and 372 g of methanol. A content of hydrolyzable chloride of 342 ppm by weight is determined in the distillate obtained. The distillation residue of about 593 g comprises predominantly siloxanes.

Example 1

2400 g of chloropropylmethyidichlorosilane and 66 g of magnesium turnings are initially introduced into the reaction vessel and are heated up to about 60° C. Methanol is now metered in over 3 hours at a metering output of 200 g/hour and over and above that at 400 g/hour. The mixture is heated up continuously to about 140° C. in the course of the reaction and the HCl gas formed is removed. After about 3 hours, the temperature falls to below 100° C. Only now is magnesium converted into magnesium chloride, hydrogen being liberated. After addition of a total of 1500 g of methanol and an after-reaction of one hour, the mixture is cooled and filtered. The crude product has a content of high-boiling components of 2% and a pH of 14. Distillation gives 2130 g (93%) of chloropropylmethyidimethoxysilane and 228 g of methanol. A content of hydrolyzable chloride of 80 ppm by weight is determined in the distillate obtained. The yellowish distillation residue of about 124 g comprises predominantly bis(3-chloropropyl-methylmethoxy) disiloxane.

Example 2

2400 g of chloropropyltrichlorosilane and 25 g of magnesium turnings are initially introduced into the reaction vessel and are heated up to about 60° C. Methanol is now metered in over 5 hours at a metering output of 200 g/hour and over and above that at 400 g/hour. The mixture is heated up continuously to about 140° C. in the course of the reaction and the HCl gas formed is removed. After about 5 hours, the temperature falls to below 100° C. After addition of a total of 1600 g of methanol and an after-reaction of one hour, 550 g of methanol are distilled off. The crude product has a content of high-boiling components of 3% and a pH of 14. It is now transferred to the distillation with the low salt content. Distillation gives 2181 g (97%) of chloropropyltrimethoxysilane and 30 g of methanol. A content of hydrolyzable chloride of 55 ppm by weight is determined in the distillate obtained. The yellowish distillation residue comprises about 67 g of bis(3-chloropropyidimethoxy) disiloxane and about 100 g of magnesium chloride.

Obviously, numerous modifications and variations of the present invention are possible in light of the above teachings. It is therefore to be understood that within the scope of the appended claims, the invention may be practiced otherwise than as specifically described herein.

This application is based on German patent application 19954635.5, filed Nov. 13, 1999, and incorporated herein by reference in its entirety.

What is claimed is:

1. A process for the preparation of alkoxysilanes, comprising:
    reacting at least one halogenosilane with at least one alcohol in the presence of metallic magnesium to form a crude product; and
    isolating an alkoxysilane from said crude product.

2. The process as claimed in claim 1, wherein said halogenosilane comprises a chlorosilane.

3. The process as claimed in claim 1, wherein said alcohol comprises at least one alcohol selected from the group consisting of methanol, ethanol, propanol, methoxyethanol, butanol and mixtures thereof.

4. The process as claimed in claim 1, wherein said alcohol is present in excess.

5. The process as claimed in claim 1, wherein said alcohol is present in an excess amount between 0.001 and 500 mol %, based on said halogenosilane.

6. The process as claimed in claim 1, wherein said metallic magnesium comprises at least one selected from the group consisting of magnesium turnings, magnesium powder, and a mixture thereof.

7. The process as claimed in claim 1, wherein said reacting is carried out at a temperature of 0 to 200° C.

8. The process as claimed in claim 1, wherein said reacting is carried out under a pressure of 0.8 to 1.3 bar absolute.

9. The process as claimed in claim 1, wherein said reacting is is carried out for a duration of 5 minutes to 48 hours.

10. The process as claimed in claim 1, wherein said crude product further comprises at least one solid, and wherein said solid is separated from said crude product is by filtration.

11. The process as claimed in claim 1, wherein said crude product further comprises at least one solid, and wherein said said alkoxysilane is separated from said solid by distillation.

12. The process as claimed in claim 1, wherein said isolating comprises distilling said alkoxysilane.

13. The process as claimed in claim 1, wherein said reacting is carried out in the substantial absence of water.

14. The process as claimed in claim 1, wherein said halogenosilane is selected from the group consisting of chlorosilane, fluorosilane, bromosilane and iodosilane.

15. The process as claimed in claim 1, wherein said halogenosilane is a chlorosilane selected from the group consisting of vinyltrichlorosilane, 3-chloropropyltrichlorosilane, 3-chloropropylmethyldichlorosilane, n-propyltrichlorosilane, i-propyltrichlorosilane, n-propylmethyldichlorosilane, trimethylchlorosilane, dimethyldichlorosilane, methyltrichlorosilane, ethyltrichlorosilane, n-butyltrichlorosilane, i-butyltrichlorosilane, i-butylmethyldichlorosilane, n-octyltrichlorosilane, hexadecyltrichlorosilane, cyclohexylmethyldichlorosilane, dicyclopentyldichlorosilane, 3-methacryloxypropyltrichlorosilane, fluoroalkyltrichlorosilane, perfluoroalkyltrichlorosilane, 3,3,4,4,5,5,6,6,7,7,8,8,8-tridecafluoro-1,1,2,2-tetrahydrooctyltrichlorosilane, 3,3,4,4,5,5,6,6,7,7,8,8,9,9,10,10,10-heptadecafluoro-1,1,2,2-tetrahydrodecyltrichlorosilane and mixtures thereof.

16. The process as claimed in claim 1, wherein said alkoxysilane is selected from the group consisting of vinyltrimethoxysilane, vinyltriethoxysilane, vinyl-tris(2-methoxyethoxy)silane, 3-chloropropyltrimethoxysilane, 3-chloropropyltriethoxysilane, 3-chloropropyl-methyldiethoxysilane, 3-chloropropylmethyldiethoxysilane, 3-propyltrimethoxysilane, n-propyltriethoxysilane, n-propylmethyldimethoxysilane, n-propylmethyldiethoxysilane, trimethylmethoxysilane, trimethylethoxysilane, dimethyldimethoxysilane, dimethyldiethoxysilane, methyltrimethoxysilane, methyltriethoxysilane, ethyltrimethoxysilane, ethyltriethoxysilane, i-butyltrimethoxysilane, i-butyltriethoxysilane, hexadecyltrimethoxysilane, hexadecyltriethoxysilane, cyclohexyl methyldimethoxysilane, cyclohexyl-methyldiethoxysilane, dicyclopentyldimethoxysilane, dicyclopentyldiethoxysilane, 3-methacryloxypropyltrimethoxysilane, 3-methacryloxypropyltriethoxysilane, perfluoroalkyl-functional alkoxysilane, fluoroalkyl-functional alkoxysilane, 3,3,4,4,5,5,6,6,7,7,8,8,8-tridecafluoro-1,1,2,2-tetrahydrooctyltrimethoxysilane, 3,3,4,4,5,5,6,6,7,7,8,8,8-tridecafluoro-1,1,2,2-tetrahydrooctyltriethoxysilane, 3,3,4,4,5,5,6,6,7,7,8,8,9,9,10,10,10-heptadecafluoro-1,1,2,2-tetrahydrodecyltrimethoxysilane, 3,3,4,4,5,5,6,6,7,7,8,8,9,9,10,10,10-heptadecafluoro-1,1,2,2-tetrahydrodecyltriethoxysilane and mixtures thereof.

* * * * *